United States Patent
Hancock et al.

(10) Patent No.: US 11,058,481 B2
(45) Date of Patent: Jul. 13, 2021

(54) RF AND/OR MICROWAVE ENERGY CONVEYING STRUCTURE, AND AN INVASIVE ELECTROSURGICAL SCOPING DEVICE INCORPORATING THE SAME

(71) Applicant: CREO MEDICAL LIMITED, Monmouthshire (GB)

(72) Inventors: Christopher Paul Hancock, Bath (GB); Malcolm White, Monmouthshire (GB); George Christian Ullrich, Gwynedd (GB); David Edward Webb, Gwynedd (GB); Shaun Preston, Monmouthshire (GB); Steven Morris, Monmouthshire (GB)

(73) Assignee: CREO MEDICAL LIMITED, Gwent (GB)

( * ) Notice: Subject to any disclaimer, the term of this patent is extended or adjusted under 35 U.S.C. 154(b) by 1128 days.

(21) Appl. No.: 15/486,110

(22) Filed: Apr. 12, 2017

(65) Prior Publication Data

US 2017/0215955 A1    Aug. 3, 2017

Related U.S. Application Data

(63) Continuation of application No. PCT/EP2015/074001, filed on Oct. 16, 2015.

(30) Foreign Application Priority Data

Oct. 17, 2014 (GB) ...................................... 1418474

(51) Int. Cl.
*A61B 18/14* (2006.01)
*A61B 18/18* (2006.01)
(Continued)

(52) U.S. Cl.
CPC .... *A61B 18/1492* (2013.01); *A61B 17/00234* (2013.01); *A61B 18/1206* (2013.01);
(Continued)

(58) Field of Classification Search
CPC .... H01R 24/38; H01R 24/58; H01R 2103/00; H01R 2201/12; A61B 18/1492;
(Continued)

(56) References Cited

U.S. PATENT DOCUMENTS 5,006,119 A    4/1991 Acker et al.
5,810,809 A *  9/1998 Rydell ............. A61B 17/32002
                                                      604/22
(Continued)

FOREIGN PATENT DOCUMENTS

JP    S60-83633 A    5/1985
JP    H03-54605 U    5/1991
(Continued)

OTHER PUBLICATIONS

Office Action issued in Japanese Patent Application No. 2017-520453 pp. 1-6, dated Jul. 11, 2019.
(Continued)

*Primary Examiner* — Michael F Peffley
*Assistant Examiner* — Amanda L Zink
(74) *Attorney, Agent, or Firm* — Arent Fox LLP (57) ABSTRACT

Embodiments of the invention provide an energy conveying structure for delivering RF and/or microwave energy to an electrosurgical instrument, where the energy conveying structure is incorporated into an insertion tube of a surgical scoping device (e.g. endoscope, laparoscope or the like). The insertion tube is a flexible conduit that is introduced into a patient's body during an invasive procedure, and can include an instrument channel and an optical channel. The energy conveying structure may be a layered coaxial struc-
(Continued)

ture that formed a liner that fits within the scoping device, e.g. within an instrument channel. Alternatively, the energy conveying structure may be a coaxial structure integrally formed as part of the flexible conduit.

23 Claims, 5 Drawing Sheets

(51) Int. Cl.
*A61B 17/00* (2006.01)
*A61B 18/12* (2006.01)
*H01R 24/38* (2011.01)
*A61B 18/00* (2006.01)
*H01R 24/58* (2011.01)
*H01R 103/00* (2006.01)

(52) U.S. Cl.
CPC ......... *A61B 18/1815* (2013.01); *H01R 24/38* (2013.01); *A61B 2017/0034* (2013.01); *A61B 2017/00477* (2013.01); *A61B 2017/00929* (2013.01); *A61B 2018/00077* (2013.01); *A61B 2018/00083* (2013.01); *A61B 2018/00178* (2013.01); *A61B 2018/00196* (2013.01); *A61B 2018/126* (2013.01); *A61B 2018/1838* (2013.01); *A61B 2018/1861* (2013.01); *A61B 2018/1892* (2013.01); *H01R 24/58* (2013.01); *H01R 2103/00* (2013.01); *H01R 2201/12* (2013.01)

(58) Field of Classification Search
CPC .......... A61B 18/1206; A61B 17/00234; A61B 18/1815; A61B 2018/00083; A61B 2018/00077; A61B 2017/00929; A61B 2017/0034; A61B 2018/1892; A61B 2018/1861; A61B 2018/1838; A61B 2018/126; A61B 2018/00196; A61B 2018/00178; A61B 2017/00477; A61B 1/018
See application file for complete search history.

(56) References Cited

U.S. PATENT DOCUMENTS

| | | | |
|---|---|---|---|
| 6,230,060 | B1 | 5/2001 | Mawhinney |
| 6,509,521 | B1 | 1/2003 | Geitz |
| 6,951,568 | B1* | 10/2005 | Chin ...................... A61B 1/018 600/104 |
| 7,150,747 | B1* | 12/2006 | McDonald ........... A61B 18/148 606/45 |
| 9,427,279 | B2* | 8/2016 | Muniz-Medina ........................... A61B 17/32002 |
| 2003/0088242 | A1 | 5/2003 | Prakash |
| 2004/0243200 | A1 | 12/2004 | Turner et al. |
| 2008/0015570 | A1 | 1/2008 | Ormsby et al. |
| 2009/0082762 | A1* | 3/2009 | Ormsby ............. A61B 18/1815 606/33 |
| 2009/0299360 | A1 | 12/2009 | Ormsby |
| 2010/0004650 | A1 | 1/2010 | Ormsby et al. |

FOREIGN PATENT DOCUMENTS

| | | | |
|---|---|---|---|
| JP | H11-128242 | A | 5/1999 |
| JP | 2002-532132 | A | 10/2002 |
| JP | 2004-518586 | A | 6/2004 |
| JP | 2005-110959 | A | 4/2005 |
| JP | 2010-540029 | A | 12/2010 |
| WO | WO 00/35363 | A1 | 6/2000 |
| WO | WO 2009/039093 | A2 | 3/2009 |
| WO | WO 2009/060213 | A1 | 5/2009 |
| WO | WO 2010/002888 | A2 | 1/2010 |

OTHER PUBLICATIONS

British Combined Search and Examination Report of related British Patent Application No. GB1518330.4 dated Mar. 16, 2016.
British Search Report of related British Patent Application No. GB1418474.1 dated Mar. 25, 2015.
International Preliminary Report on Patentability of related International Patent Application No. PCT/EP2015/074001 dated Feb. 2, 2017.
International Search Report and Written Opinion of related International Patent Application No. PCT/EP2015/074001 dated Dec. 17, 2015.
Written Opinion of related International Patent Application No. PCT/EP2015/074001 dated Sep. 8, 2016.

* cited by examiner

RF AND/OR MICROWAVE ENERGY CONVEYING STRUCTURE, AND AN INVASIVE ELECTROSURGICAL SCOPING DEVICE INCORPORATING THE SAME

CROSS-REFERENCE TO RELATED APPLICATIONS

This application is a Continuation of International Patent Application No. PCT/EP2015/074001, filed Oct. 16, 2015, which claims priority to Great Britain Patent Application No. 1418474.1, filed Oct. 17, 2014. The disclosures of the priority applications are incorporated in their entirety herein by reference.

FIELD OF THE INVENTION

The invention relates to an energy conveying structure (e.g. waveguide or cable) for carrying radiofrequency (RF) and/or microwave energy from an electrosurgical generator to an electrosurgical instrument. In particular, the invention concerns electrosurgical instruments that are used in invasive procedures, e.g. introduced through an instrument channel of an endoscope, laparoscope or the like. For example, the invention may find particular use in natural orifice transluminal endoscopic surgery (NOTES).

BACKGROUND TO THE INVENTION

Electrosurgical instruments are instruments that are used to deliver radiofrequency and/or microwave frequency energy to biological tissue, for purposes such as cutting biological tissue or coagulating blood. Radiofrequency and/or microwave frequency energy is typically supplied to the electrosurgical instrument using a cable. Conventional cables used for this purpose have a coaxial transmission line structure comprising a solid or multi-wire cylindrical inner conductor, a tubular layer of dielectric material around the inner conductor, and a tubular outer conductor around the dielectric material.

When operating many electrosurgical instruments it is common to need to provide additional supplies or components (e.g. control means) to the electrosurgical instrument, such as a liquid or gas feed, liquids or gases, or guide- or pull-wires for manipulating (for example opening/closing, rotating or extending/retracting) part(s) of the electrosurgical instrument.

In order to provide these additional supplies or components to the electrosurgical instrument, additional structures have been provided together with the conventional cable, such as additional tubes adjacent to the conventional cable. For example, it is known to provide an additional tube housing a pull-wire for the electrosurgical instrument alongside the conventional cable, and to house the conventional cable and the tube housing the pull-wire within a single protective jacket/casing.

Typically, the diameter of an instrument channel of a scoping device (e.g. endoscope or laparoscope) is less than 3 mm, e.g. 2.8 mm. It is an ongoing challenge to provide both sufficient power and the additional supplies or components mentioned above in a compact enough form to fit within an instrument channel whilst maintaining flexibility and restricting power loss to acceptable (i.e. safe) levels.

WO 00/35363 discloses catheter system for RF ablation that comprises a hollow coaxial structure.

U.S. Pat. No. 6,230,060 discloses a balloon catheter system that comprises a hollow coaxial structure.

US 2003/0088242 discloses a microwave antenna assembly.

SUMMARY OF THE INVENTION

At its most general, the present invention proposes to incorporate an energy conveying structure for an electrosurgical instrument into an insertion tube of a surgical scoping device (e.g. endoscope, laparoscope or the like). The insertion tube is the flexible conduit that is introduced into a patient's body during an invasive procedure. Typically it includes an instrument channel and an optical channel (for transmitting light to illuminate and/or capture images of a treatment site at the distal end of the insertion tube. The instrument channel may have a diameter suitable for receiving invasive surgical tools. The diameter may be the same as found in conventional surgical scoping devices, e.g. 1 mm or more, preferably 1.4 mm or more, preferably 2.8 mm or more, preferably 3.2 mm or more. The diameter is preferably no more than 5 mm, e.g. in the range 1 to 5 mm, or 1.4 to 5 mm, or 2.8 to 5 mm, or 3.2 mm to 5 mm.

In the invention, the energy may thus be conveyed through the insertion tube to an electrosurgical instrument independently of any control line or feed line that runs to the electrosurgical instrument through the instrument channel. Accordingly, the invention may increase the space available for additional supplies (e.g. fluid feeds) or components (e.g. control wires) to be used with the electrosurgical instrument. Moreover, the invention may reduce or eliminate the effect that such additional supplies or components have on the conveyed energy.

The invention may provide the energy conveying structure around the instrument channel within the wall of the insertion tube itself, or as a liner (e.g. a detachable cover) for the instrument channel, or as a combination of the two.

By providing the energy conveying structure outside the instrument channel, the invention permits larger diameter conductive (e.g. coaxial) structures to be used. These structures may have a lower loss than conventional smaller diameter cables, which in turn may enable more power to be safely delivered to the electrosurgical instrument.

According to an aspect of the present invention there is provided an energy conveying structure for invasive electrosurgery, the energy conveying structure comprising a coaxial layered structure having: an innermost insulating layer; an inner conductive layer formed on the innermost insulating layer; an outer conductive layer formed coaxially with the inner conductive; and a dielectric layer separating the inner conductive layer and the outer conductive layer, wherein the inner conductive layer, the outer conductive layer and the dielectric layer form a transmission line for conveying radiofrequency (RF) and/or microwave energy, wherein the coaxial layered structure is insertable in a flexible insertion tube of an invasive surgical scoping device (e.g. endoscope, laparoscope or the like), and wherein the innermost insulating layer is hollow to form an instrument channel for the invasive surgical scoping device.

The diameter of the instrument channel formed in the innermost insulating layer is preferably 3 mm or less, e.g. 2.8 mm.

The energy conveying structure may include, e.g. at a distal end thereof, a first terminal that is electrically connected to the inner conductive layer and which extends through the innermost insulating layer into the instrument channel, and a second terminal that is electrically connected to the outer conductive layer and which extends through the dielectric layer and innermost insulating layer into the instrument channel. The first terminal and the second terminal may be arranged to form electrical connection (e.g. physically engage) corresponding contacts formed on an electrosurgical instrument that is insertable in or through the instrument channel. The first terminal and the second terminal may be formed at the distal end of the inner conductive layer and outer conductive layer respectively. The outer conductive layer may extend longitudinally further in a distal direction than the inner conductive layer, whereby the first terminal is located proximally from the second terminal.

Herein, the term "inner" means radially closer to the centre (e.g. axis) of the instrument channel. The term "outer" means radially further from the centre (axis) of the instrument channel.

The term "conductive" is used herein to mean electrically conductive, unless the context dictates otherwise.

Herein, the terms "proximal" and "distal" refer to the ends of the energy conveying structure further from and closer to the treatment site respectively. Thus, in use the proximal end is closer to a generator for providing the RF and/or microwave energy, whereas the distal end is closer to the treatment site, i.e. the patient.

An electrosurgical instrument may be any instrument, or tool, which is used during surgery and which utilises RF or microwave energy. Herein, radiofrequency (RF) may mean a stable fixed frequency in the range 10 kHz to 300 MHz and microwave energy may mean electromagnetic energy having a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include 915 MHz, 2.45 GHz, 5.8 GHz, 14.5 GHz, 24 GHz.

The instrument channel formed by the innermost insulating layer may act as a conventional instrument channel, e.g. to receive a catheter that conveys an electrosurgical instrument to the distal end thereof. The catheter may be a hollow tube for carrying other components needed in use of the electrosurgical instrument, such as a gas or liquid feed, or a pull-wire or other control means, can be fed up through the inside of the catheter. By providing the energy conveying structure in the wall of the instrument channel, the invention may maximise the space available for these components.

The coaxial layered structure may form a liner that is receivable in the flexible insertion tube of the surgical scoping device. In one embodiment, the outer conductive layer and a portion of the dielectric layer may be formed directly (e.g. permanently) on an inner surface of a longitudinal bore through the flexible insertion tube. In this case, the liner may comprise a coaxial structure comprising the innermost layer, the inner conductive layer and another portion of the dielectric layer. The liner may be insertable into the longitudinal bore to fit snugly against She portion of the dielectric layer formed therein. Thermal effects may be used to contract and expand the liner to create a snug fit without air gaps.

The liners discussed above may be single or multi-use. An advantage of forming the energy conveying structure partly in the flexible insertion tube and partly as a liner is that it facilitates fabrication and assembly, especially in cases where both conductive layers are covered (protected) during assembly.

In another aspect of the invention, the energy conveying structure may be fabricated as an integral part of the flexible insertion tube, i.e. a permanent component of the surgical scoping device.

The flexible insertion tube may include a stop flange at its distal end, the stop flange having a projection that overhangs the entrance to the instrument channel to limit the extent to which the electrosurgical instrument can be pushed out of the distal end. The flexible insertion tube may also have a resilient seal mounted over the entrance to the instrument channel. The resilient seal may comprise an annular membrane that is deformable to admit the electrosurgical instrument to pass out of the instrument channel but to prevent the ingress of matter from the treatment site back into the instrument channel.

The electrosurgical instrument may comprise a first conductive element and a second conductive element at its distal end, which together for a bipolar transmission structure for delivering RF and/or microwave energy into biological tissue at the treatment site. As discussed above, it may be desirable to connect the energy conveying structure to the electrosurgical instrument in order to convey RF and/or microwave energy to the bipolar transmission structure. To achieve this connection, the electrosurgical instrument may include a connection collar having a first contact for connecting to the first terminal and a second contact for connecting to the second terminal. The first contact and the second contact may be electrically connected to the first conductive element and the second conductive element respectively.

The electrosurgical instrument may be introduced to the distal end of the instrument channel via a catheter that is fed through the instrument channel. The connection collar may be mounted on the catheter, and may comprise a cylindrical body having a diameter greater than the diameter of the catheter. The outer surface of the cylindrical body may be in close proximity (e.g. touching) the innermost layer of the energy conveying structure, to ensure secure engagement between the first contact and first terminal and between the second contact and second terminal. The first terminal and second terminal may project inwards from the innermost layer slightly. The connection collar may include a shoulder for abutting the stop flange to securely locate the collar in position.

The electrosurgical instrument may include an extension sleeve that extends axially away from the connection collar towards the bipolar transmission structure at the distal end of the electrosurgical instrument. In use, the extension sleeve may thus protrude out of the end of the instrument channel. The extension sleeve may comprise a tube of dielectric material, and may carry conductive structures (e.g. conductive rods or the like) which provide electrical connection between the first contact and first conductive element and between the second contact and second conductive element respectively. The conductive structure may comprise a short length of conventional coaxial cable.

If the electrosurgical instrument is arranged to receive microwave energy from the energy conveying structure, it may be desirable for the electrosurgical instrument to be configured to match the impedance of the energy conveying structure with the impedance of the electrosurgical instrument at the frequency of microwave energy. This may be achieved by selecting the geometry (e.g. sizes and/or shapes) of the first and second terminals, the connection collar and the connection between the conductive structure of the extension sleeve and the bipolar transmission structure, e.g. based on microwave field simulations, experimental measurements, etc. Providing an impedance match reduces or eliminates power reflections at transition points between different geometries in the energy conveying path, and thus may enable power to be delivered more efficiently to the electrosurgical instrument. The conductive structure in the extension sleeve may have an electrical length of a multiple of half a wavelength of the microwave energy to render it effectively invisible in any impedance matching geometry.

If the electrosurgical instrument is arranged to receive RF energy from the energy conveying structure, it may be desirable to prevent voltage breakdown from occurring between the inner conductive layer and outer conductive layer. This may be achieved by using a material with a high breakdown threshold (e.g. Kapton® polyimide tape) as the dielectric layer. Alternatively, if the electrosurgical instrument is arranged to receive both RF energy and microwave energy from the energy conveying structure, it may be desirable to create separate pathways for the RF energy and microwave energy, because low loss dielectric material suitable for supporting microwave energy propagation may not have a high enough breakdown threshold to safely insulate conductors carrying RF energy. Accordingly, the energy conveying structure may be include an additional conductor which forms a first pole of an RF-carrying bipolar transmission line, and wherein the inner conductive layer and the outer conductive layer form a second pole of the RF-carrying bipolar transmission line. For example the additional conductor may be a conductive wire carried within the instrument channel. In this arrangement, the innermost insulating layer may be made of a material (e.g. polyimide) with the required breakdown properties. Where an additional conductor is provided to carry the RF energy, the inner conductive layer and outer conductive layer of the energy conveying structure may be electrically connected (shorted) at the proximal end thereof.

The additional conductor positioned in the instrument channel may be a conductive rod or tube used specifically for this purpose. Alternatively, an additional component being passed through the instrument channel may be function as the additional conductor. For example, a tube used to supply liquid or gas to the electrosurgical instrument, or a housing for a guide- or pull-wire may be formed of, or coated with, a conducting material and may act as the additional conductor. A generator may then be used to input a radiofrequency signal into the cable using the outer conductive layer (or inner conductive layer) and the additional conductor separately from a microwave frequency signal, which is input to the inner conductive layer and outer conductive layer. The electrosurgical instrument may include a dedicated contact or port for electrically connecting to the additional conductor.

With an arrangement such as this it may be necessary to provide a configuration, such as a diplexer, at the distal end of the energy conveying structure to prevent the higher voltage radiofrequency signal from travelling back along the inner conductive layer and outer conductive layer, and/or to prevent the microwave signal from travelling back along the additional conductor.

The dielectric layer may comprise a solid tube of dielectric material or a tube of dielectric material having a porous structure. Being a solid tube of dielectric material may mean that the dielectric material is substantially homogeneous. Having a porous structure may means that the dielectric material is substantially inhomogeneous, with a significant number or amount of air pockets or voids. For example, a porous structure may mean a honeycomb structure, a mesh structure, or a foam structure. The dielectric material may comprise PTFE, or another low-loss microwave dielectric. The dielectric material may comprise a tube with a wall thickness of at least 0.2 mm, preferably at least 0.3 mm, more preferably at least 0.4 mm, e.g. between 0.3 and 0.6 mm.

The inner conductive layer and/or the outer conductive layer may comprise: a metal coating on the inside or outside of a tube of material; a solid tube of metal positioned against the inside or outside of a tube of material; or a layer of braided conductive material embedded in a tube of material. The inner conductive layer and/or the outer conductive layer may comprise a silver coating. The inner conductive layer and/or the outer conductive layer may have a thickness of approximately 0.01 mm.

Instead of being projections, one or both of the first terminal and the second terminal may comprise a recess, e.g. formed in the innermost insulating layer. The connection collar (discussed above) for example formed in an end face of the cable, for receiving a corresponding conductive protrusion on an end face of the electrosurgical instrument.

In one configuration the energy conveying structure may be fabricated as a plurality of layers, e.g. a hollow inner tubular layer (the innermost layer); a layer of conductive material on an outer surface of the hollow inner tubular layer (inner conductive layer); a tube of dielectric material on an outer surface of the conductive material (dielectric layer; and a layer of conductive material on an outer surface of the tube of the dielectric material (outer conductive layer). The structure may, or may not, comprise air gaps between some or all of these layers. An advantage of avoiding air gaps is that losses in the cable may be minimised. In one example, this structure could be manufactured by sequentially coating each subsequent layer over the preceding (inner) layer. Alternatively, this structure could be made by forming one or more of the layers as a first part and one or more of the layers as a second part, and then sliding one part inside of the other. The hollow inner tubular layer preferably comprises polyimide, but may be PTFE or other suitable insulating material. The hollow inner tubular layer may have a thickness of 0.1 mm.

By providing an energy conveying structure within the walls of an instrument channel of an invasive surgical scoping apparatus, the invention may allow both electrosurgical and non-electrosurgical instruments. In other words, the invasive surgical scoping device may be operable in a conventional (non-electrosurgical) manner.

BRIEF DESCRIPTION OF THE DRAWINGS

Examples of the invention as discussed in detail below with reference to the accompanying drawings, in which.

DETAILED DESCRIPTION; FURTHER OPTIONS AND PREFERENCES

Figure 1:
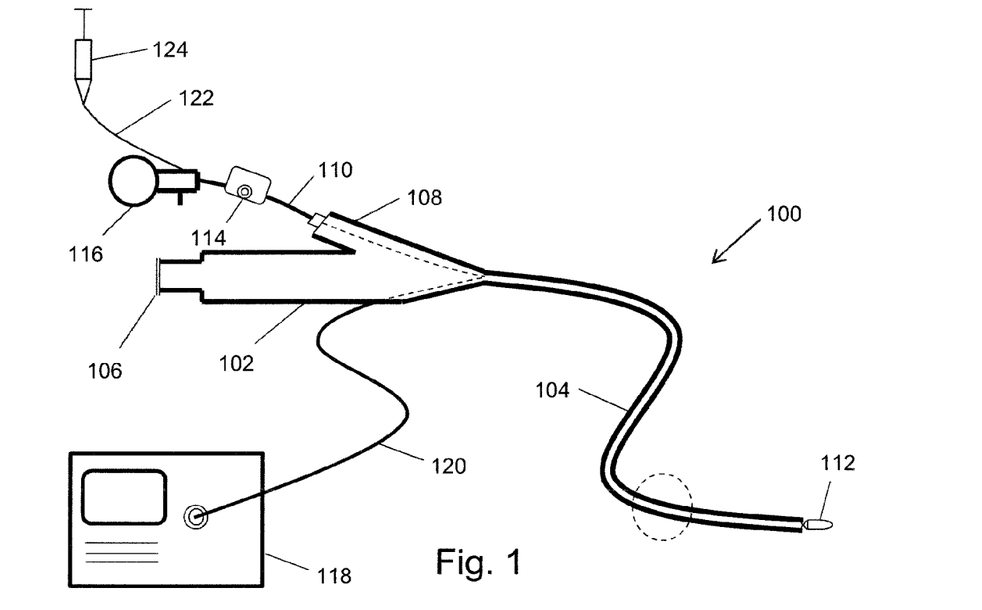
FIG. 1 is a schematic diagram of an electrosurgical system for an invasive procedure in which an energy conveying structure according to the invention can be used.

FIG. 1 is a schematic view of an invasive electrosurgical system 100 in which the present invention may be used. The system 100 comprises an endoscope that has a main body 102 and a flexible insertion tube 104 extending from the main body 102, which is suitable for insertion into the body to access the treatment site. The insertion tube 104 houses various channels, e.g. an instrument channel and an observation channel. The observation channel may carry optical equipment suitable for delivering an image of the treatment site to an observation port 106. The instrument channel 104 may include means for conveying radiofrequency (RF) and/or microwave energy. An electrosurgical generator 118 is connected to the main body 102 via a cable 120 which carries the RF and/or microwave energy into the main body 102 and is electrically connected to the energy conveying means in the instrument channel. This electrical connection may be provided by a "T" connection between a coaxial cable from the generator and the transmission line of the energy conveying structure. Preferably there is a filter or choke between the "T" junction and an instrument port on the generator to prevent microwave leakage to the instrument port. This must be placed at half a wavelength at the microwave frequency from the "T" junction so that the "T" junction has a high return loss, i.e. does not reflect a significant proportion of the microwave energy back to the generator. The proximal end of the transmission line in the energy conveying structure is open circuit if RF energy is to be transmitted so as not to short out the RF voltage. It is also insulated and protected so that it does not break down for RF voltages or expose the operator to high RF voltages.

The main body 102 includes an instrument port 108 for receiving an electrosurgical instrument into the instrument channel. The electrosurgical instrument comprises a flexible catheter 110 which has at its distal end an instrument tip 112 that is arranged to receive the RF and/or microwave energy from the energy conveying means in the flexible insertion tube 104. The instrument tip 112 includes an energy delivery portion for delivering the receiving RF and/or microwave energy into biological tissue, e.g. to assist in treatment, e.g. cutting or coagulation.

The catheter 110 is connected at its proximal end to a rotator 114, which acts to rotate the catheter (and therefore the instrument tip 112) relative to the instrument channel. The catheter 110 may contain one of more control wires, e.g. pull/push rods or the like. The control wires may pass out of the proximal end of the catheter to engage a slider 116, which operates to extend and retract the control wires to effect action at the instrument tip.

In this embodiment, the catheter 110 is further arranged to receive a flexible fluid feed pipe 122 that is connected to a fluid delivery mechanism 124 (e.g. a syringe or pump, which can be manually or automatically operated). The flexible fluid feed pipe 122 may extend, e.g. within or alongside the catheter 110, through the instrument channel of the flexible insertion tube 104. The instrument tip 112 may include a fluid delivery port (not shown), e.g. a retractable needle, in fluid communication with the flexible fluid feed pipe 122. The fluid delivery port may be operable to deliver fluid (e.g. saline) to the treatment site, e.g. to flush or clean the area, or to be injected into tissue, e.g. to plump up a sessile polyp as a preliminary step in a polypectomy procedure.

The fluid feed pipe 122 may terminate at a sealed junction at a proximal end of the catheter 110. In this arrangement the catheter 110 itself may provide a fluid flow path for the fluid between the proximal end and the instrument tip 112. In this arrangement, the instrument tip may provide a sealed junction at a distal end of the catheter 110, and the fluid delivery port may include a proximal inlet (which may be opened and closed by an operator) in fluid communication with the inside of the catheter 110 in order to create the fluid flow path to the treatment site.

According to the invention, there is an energy conveying structure in the flexible insertion tube 104, e.g. in the walls of the instrument channel, for carrying the RF and/or microwave energy to the instrument tip 112. This arrangement has two advantages. Firstly, it means that the catheter 110 does not need to carry a cable or other energy conveying means. As a result there is more space for carrying control wires, fluid, etc. to the instrument tip 112, and moreover the presence of the control wires, fluid has no effect on the RF and/or microwave energy. Secondly, this arrangement enables the energy conveying structure to have a larger size that would be necessary if it were to fit within the catheter. As a result the energy conveying structure can have a lower loss than in conventional electrosurgical systems, which in turn enables more power to be safely delivered to the instrument tip 112.

Figure 2:
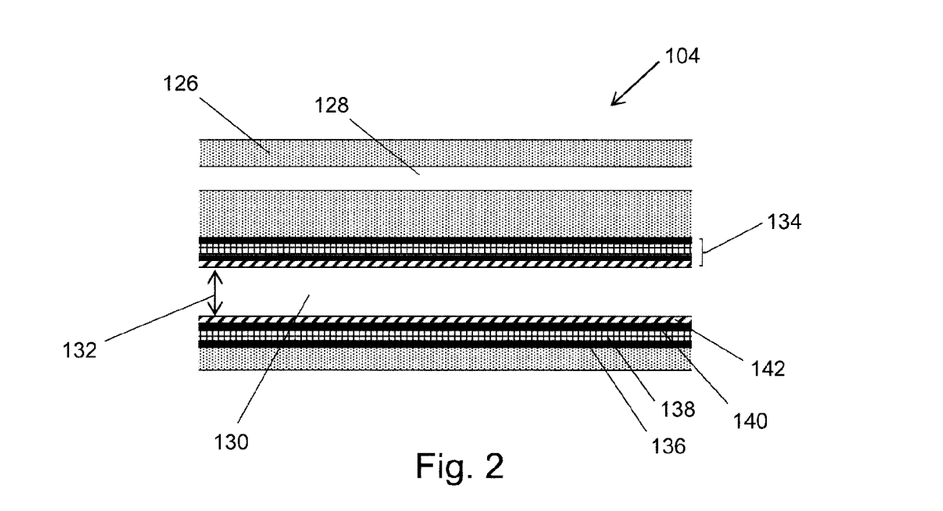
FIG. 2 is a cross-sectional view through an insertion tube of an endoscope that is an embodiment of the invention.

FIG. 2 is a schematic cross-sectional view through a short portion of the flexible insertion tube 104 shown in FIG. 1. The scale of some features in the drawing has been exaggerated for clarity. The flexible insertion tube 104 is formed of a resiliently deformable cylindrical member 126 which has at least two longitudinal passages formed therethrough. A first passage forms an observation channel 128, through which an optical fibre bundle may pass to deliver light and/or return captured images. A second passage forms an instrument channel 130, through which the catheter 110 discussed above passes. The instrument channel 130 may have a diameter 132 of 3 mm or less, e.g. 2.8 mm.

In conventional scoping devices, the inner surface of the instrument channel was formed by the resiliently deformable cylindrical member 126. However, according to the invention, the flexible insertion tube 104 includes a wall 134 around the instrument channel 130 that is formed from a plurality of layers which act as an energy conveying structure, which in this example is an coaxial energy conveying structure.

The wall 134 comprises an outer conductive layer 136, e.g. formed from silver or silver-plated copper, a dielectric layer 138 (e.g. formed from PTFE or other suitable flexible low loss material) in contact with the inner surface of the outer conductive layer 136, an inner conductive layer 140, e.g. formed from silver or silver-plated copper, in contact with the inner surface of the dielectric layer 138, and an insulating innermost layer 142, e.g. formed from polyimide or PEEK, in contact with the inner surface of the inner conductive layer 140.

The outer conductive layer 136 and the inner conductive layer 140 have a thickness greater than the skin depth of the microwave energy that they are to convey, but still thin enough to allow the insertion tube 104 to flex. For example the outer conductive layer 136 and the inner conductive layer 140 may be formed from foil or braided material.

The outer conductive layer 136, the inner conductive layer 140 and the dielectric layer 138 that separates them together form a coaxial structure suitable for conveying RF and/or microwave energy. In some embodiments, the energy conveying structure may be used only to convey RF energy. In such arrangements, it is desirable to prevent voltage breakdown between the outer conductive layer 136 and the inner conductive layer 140. In such RF-only examples, the dielectric layer 138 may preferably be formed from a dielectric with a high breakdown strength. For example, Kapton® polyimide film may be used, which as a breakdown strength of 118 kVmm$^{-1}$ in the sub-mm thickness range.

Where microwave energy is to be delivered, it is desirable for the dielectric layer 138 to exhibit low loss at the frequency of the microwave energy. For example, at 5.8 GHz PTFE is a suitable low loss dielectric.

Figure 3A:
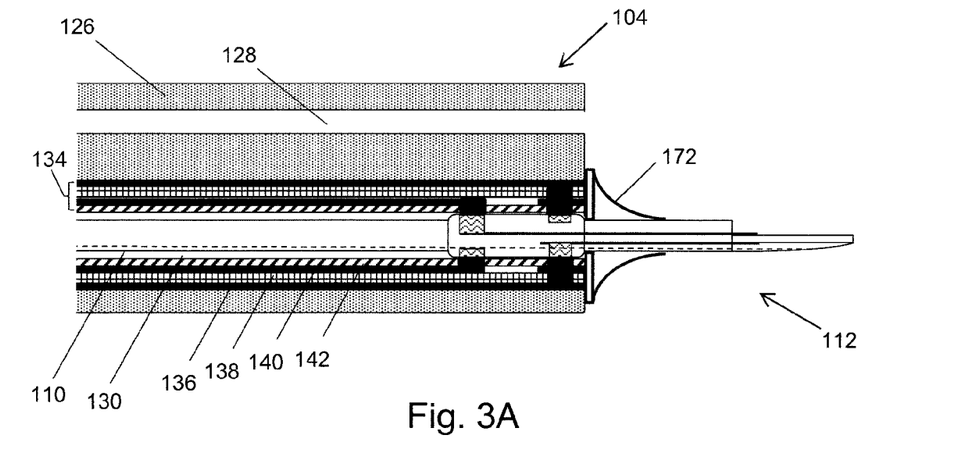
FIG. 3A is a cross-sectional view though a distal tip portion of an endoscope that is an embodiment of the invention with an electrosurgical instrument in an instrument channel thereof.

FIG. 3A is a schematic diagram of the distal end of the flexible insertion tube 104 shown in FIG. 2, now with a catheter 110 and instrument tip 112 inserted in the instrument channel 130.

Figure 3B:
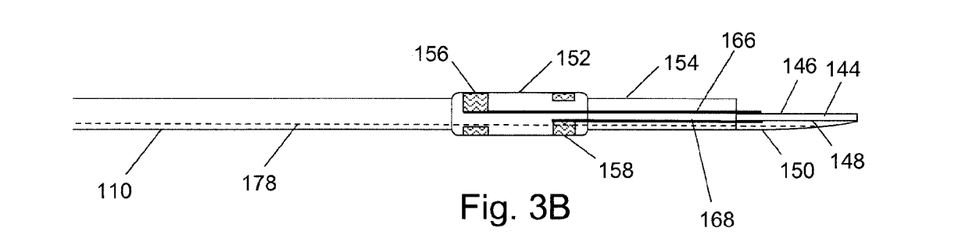
FIG. 3B is a cross-sectional view of only the electrosurgical instrument shown in FIG. 3A.

The instrument tip 112, which is shown alone in FIG. 3B, comprises a connection collar 152 attached to the distal end of the catheter 110, an extension sleeve 154 which extends distally from the connection collar 152, and a resection instrument connected at a distal end of the extension sleeve 154. The resection instrument is formed from a piece of rigid dielectric 144 that has a conductive coating (not shown) on its upper surface 146 and lower surface 148 and a smooth tapering dielectric 150 formed below the lower surface 148.

The connection collar 152 comprises a short rigid cylindrical portion having a diameter selected to snugly fit in the instrument channel so that its outer surface is in physical contact with the surface that defines the instrument channel 130 (i.e. the inner surface of wall 134). The connection collar 152 may have a larger diameter than the catheter 110.

A pair of contacts 156, 158 are formed on the outer surface of the connection collar 152. The contacts 156, 158 may extend around all or part of the outer surface. In this embodiment, a back (i.e. proximal) contact 156 is arranged to electrically connect to the inner conductive layer 140 of the energy conveying structure in the wall 134 of the instrument channel 130, and a forward (i.e. distal) annular contact 158 is arranged to electrically connect to the outer conductive layer 136 of the energy conveying structure in the wall 134 of the instrument channel 130.

Figure 3C:
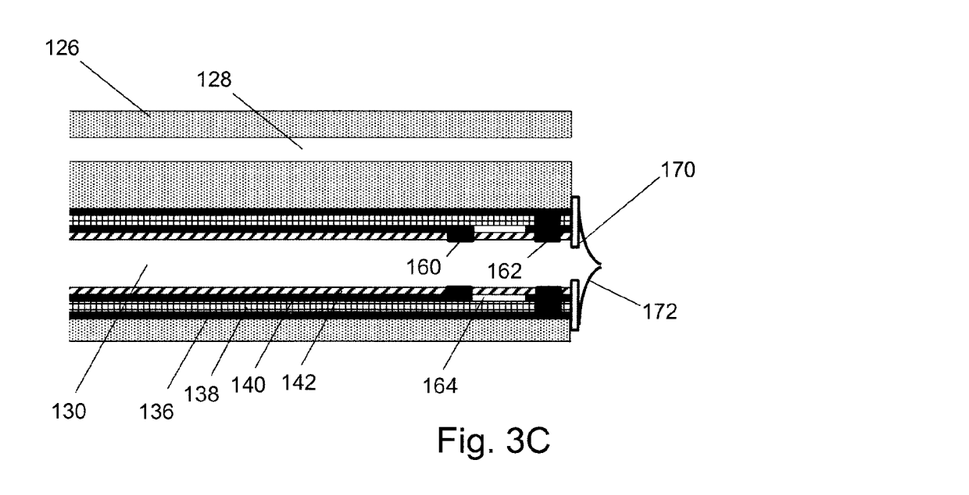
FIG. 3C is a cross-sectional view of only the distal tip portion of the endoscope shown in FIG. 3A.

To achieve these electrical connections, the wall 134 has a pair of longitudinally spaced terminals 160, 162 that protrude through the innermost layer 142 at the distal end of the instrument channel 130, as shown in FIG. 3C. The terminals 160, 162 may extend around all or part of the inner surface of the instrument channel 130. In this embodiment, a back (i.e. proximal) terminal 160 extends through the innermost layer 142 from a distal end of the inner conductive layer 140, and a forward (i.e. distal) terminal 162 extends through both the dielectric layer 138 and the innermost layer 142 from a distal end of the outer conductive layer 136.

The outer conductive layer 136 extends longitudinally beyond a distal end of the inner conductive layer 140. The inner conductive layer 140 thus terminates at the back terminal 160, i.e. there is a gap 164 (e.g. an air gap or other insulating material) located beyond of the distal end of the inner conductive layer 140 before the forward terminal 162.

A conductive rod 166 extends from the back contact 156 through the extension sleeve 154 to provide an electrical connection for the conductive coating on the upper surface 146 of the piece of rigid dielectric 144. The upper surface 146 is therefore electrically connected to the inner conductive layer 140 of the energy conveying structure in the wall 134 of the instrument channel 130. Similarly, a conductive rod 168 extends from the forward contact 158 through the extension sleeve 154 to provide an electrical connection for the conductive coating on the lower surface 148 of the piece of rigid dielectric 144. The lower surface 148 is therefore electrically connected to the outer conductive layer 136 of the energy conveying structure in the wall 134 of the instrument channel 130.

The extension sleeve 154 may be a rigid tube of dielectric material for both protecting and electrically insulating the conductive rods 166, 168. The length of the extension sleeve 154 may be chosen to enable the instrument to protrude a useful distance from the distal end of the instrument channel 130. The extension sleeve 154 may have an electric length that corresponds to half a wavelength of the microwave energy that is conveyed by the extension sleeve 154. The conductive rods 166, 168 may be separately enclosed (e.g. coated of otherwise covered) by dielectric, e.g. glue, plastic or some other insulator, to prevent breakdown, especially where they are close together.

A distal end of the connection collar 152 may abut against a stop flange 170 formed at the distal end of the instrument channel 130. The instrument tip 112 can therefore be secured in place with an electrical connection between the contacts 156, 158 and terminals 160, 162, e.g. by maintaining a pushing force on the catheter 110. Although in this embodiment the connection collar 152 performs a dual function of electrical connection and physical stop, it is possible for these functions to be performed by separate features, in which case the connection collar 152 may be located further back in the instrument channel 130 and the extension sleeve 154 may be longer.

To prevent material from the treatment site escaping backwards into the instrument channel, a seal 172 may be formed over the entrance to the instrument channel 130. The seal 172 may comprise a resilient flap through which the instrument can be pushed but which closes to form a fluid tight cover when the instrument is removed (as shown in FIG. 3C).

The catheter 110 may be a hollow tube for conveying control lines or a fluid feed 178 to the instrument. In this embodiment, the fluid line extends right through to the distal end of the instrument, e.g. for delivering saline to the treatment site.

In practice, it may be desirable to form the wall 134 separately from the flexible insertion tube 104, e.g. as an insertable single-or multiple-use liner that can be introduced into the flexible insertion tube 104 in a separate assembly step.

Figure 4A:
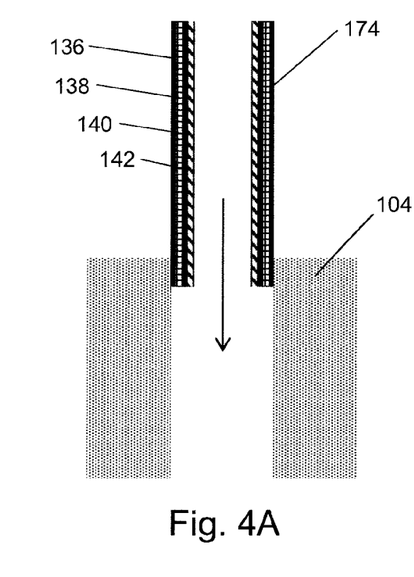
FIG. 4A is a schematic diagram showing energy conveying liner for an endoscope that is an embodiment of the invention.

FIG. 4A is a schematic cross-sectional diagram showing a first example of such a liner 174 being inserted into a flexible insertion tube 104. In this example the liner 174 has the same structure as the wall 134 described above. In particular, the internal channel through the liner 174 has the required dimensions of the instrument channel (e.g. a diameter of 2.8 mm). The liner may be formed by extruding the innermost layer 142, coating the outer surface thereof with conductive material to form the inner conductive layer 140, extruding or otherwise forming the dielectric layer 138 on the outer surface of the inner conductive layer 140, and finally coating the outer surface thereof with conductive material to form the outer conductive layer 136. The liner 174 may be secured to flexible insertion tube by interference fit, e.g. by using thermal effects to cause the liner 174 to expand and fit tightly within the available space.

Figure 4B:
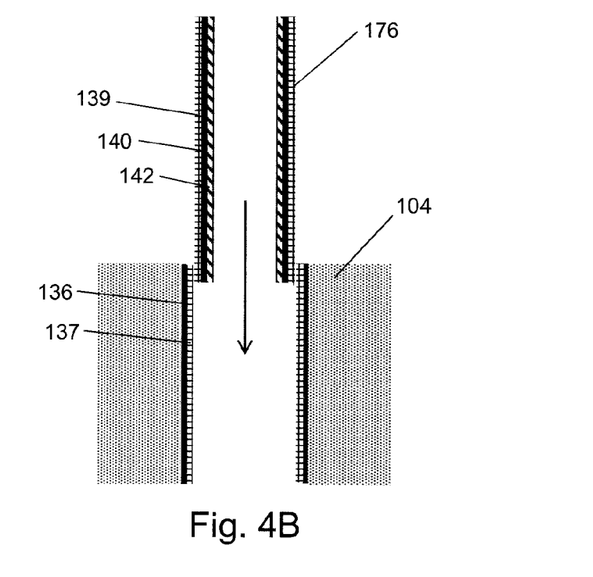
FIG. 4B is a schematic diagram showing another energy conveying liner for an endoscope that is an embodiment of the invention.

FIG. 4B is a schematic cross-sectional diagram showing a second example of a liner 176 being inserted into a flexible insertion tube 104. In this example, part of the wall 134 is formed (e.g. permanently) in the insertion tube 104 and part is inserted as a liner 176. Thus, the inner surface of a longitudinal passageway in the flexible insertion tube 104 may be coated with conductive material to form the outer conductive layer 136. A layer of dielectric 137 may be formed, e.g. extruded on the inner surface of the outer conductive layer 136. Separately, the liner 176 may be formed by extruding the innermost layer 142, coating the outer surface thereof with conductive material to form the inner conductive layer 140, and extruding or otherwise forming a dielectric layer 139 on the outer surface of the inner conductive layer 140. When the liner 176 is inserted into the flexible insertion tube 104, the dielectric layers 136, 137 physically engage each another to form a single dielectric layer that performs the same function as the dielectric layer 138 discussed above. This example may be desirable because it avoided exposing the conductive layers during assembly, which may therefore reduce the risk of damage.

Figure 5:
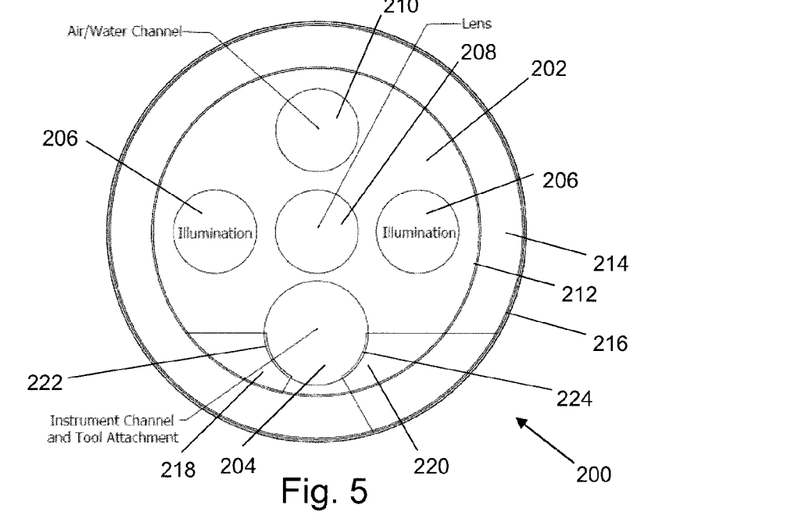
FIG. 5 is a schematic cross-sectional view of an endoscopic insertion tube that has a coaxial energy conveying structure integrally formed therein.

FIG. 5 shows another embodiment of the invention, in which a coaxial energy conveying structure, e.g. a coaxial transmission structure is incorporated into the outer layers of a insertion tube of an endoscope. FIG. 5 is a cross-sectional view of an endoscopic insertion tube 200. The insertion tube 200 comprising a main tubular body 202 in which are formed the instrument channel 204, two illumination channels 206, an optical channel 208 and a fluid channel 210. A coaxial transmission line is formed outside the main tubular body 202. The coaxial transmission line comprises an inner conductor 212 formed on the outer surface of the main tubular body 202, a layer of dielectric material 214 on the inner conductor 212, and an outer conductor 216 on the dielectric material 214. This information concerns the design and development of a larger diameter super cable suitable for use in this application. The outer conductor 216 may be have a protective layer formed thereon.

The outer diameter of the coaxial transmission line in this embodiment can thus correspond to the typical outer diameter of the insertion tube. Different types of scoping device can have different outer diameters. Depending on the type of scoping device, the outer diameter of the coaxial transmission line may be in a range of 5 mm to 20 mm. As discussed below, the thickness of the dielectric material may be determined based on the outer diameter to achieve an optimal (i.e. minimal) loss. The insertion tube may have a length up to 2.35 m.

FIG. 5 shows schematically how the coaxial transmission line may be electrically connected to a tool mounted in the instrument channel 204. Both the inner conductor 212 and the outer conductor 216 will have respective radial connector portions 218, 220 that travel into the device to electrically attach to a first pad 222 (for the inner conductor) and an second pad 224 (for the outer conductor) that are exposed in the instrument channel 204.

The tool can then be affixed into the instrument channel 204 and energy provided through the first pad 222 and second pad 224. The instrument channel can still be used as in a normal endoscope if the tool does not need electrical power. In order to avoid shorting the conductors, the first pad and second pad may be at different axial positions along the instrument channel, as discussed above. Preferably they are electrically insulated from each other, e.g. by providing an insulating material on the inner surface of the instrument channel between the first and second pads. Depending on the geometry, the insulating material may be the same as the dielectric material 214. If a higher strength material is required, then a Kapton® material could be used.

Figure 6:
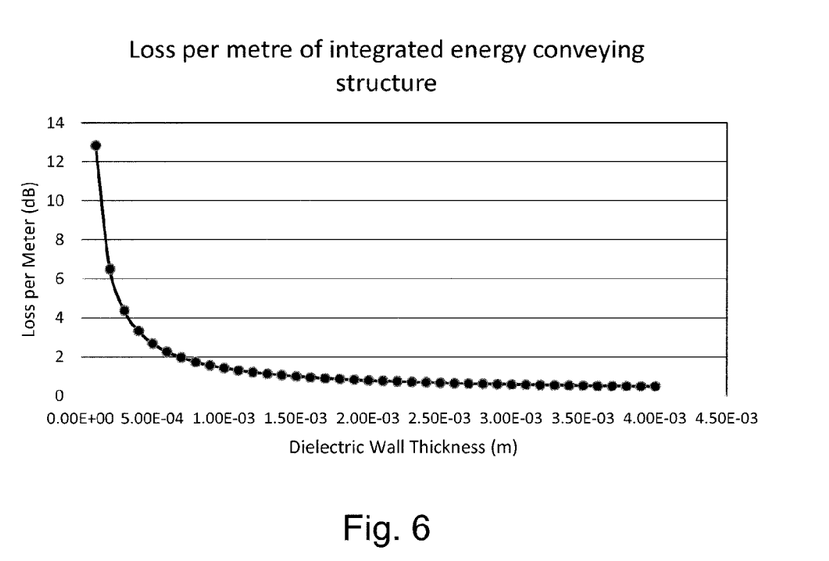
FIG. 6 is a graph showing how loss per meter along a coaxial energy conveying structure varies with the thickness of a dielectric wall separating coaxial inner and outer conductors.

FIG. 6 shows a graph of loss per metre in the coaxial transmission line structure discussed with reference to FIG. 5 as a function of the thickness of the dielectric material 214. This shows that for a given outer diameter, the conductor loss falls off at first as the thickness increases but eventually flattens off to a limit. For this data an assumption has been made that the inner diameter of the outer conductor is 10 mm giving a device of approximately 10.3 mm diameter when including the 0.5 mm thick conductor and 1 mm thick protective jacket. It has also been assumed that the dielectric material is low density PTFE with a dielectric constant of 2.1 and tan delta of 0.0002 at 5.8 GHz.

In general the total loss can be determined based on the geometry of the transmission line. As the conductors get larger, the insertion loss should decrease due to the resistance. Similarly as more dielectric material is used the losses decrease. The larger the distance between conductors the higher the impedance. As dielectric thickness increases, there is less loss, higher impedance due to the conductor geometry and greater dielectric strength (i.e. the structure can withstand a higher voltage before breakdown).

Figure 7:
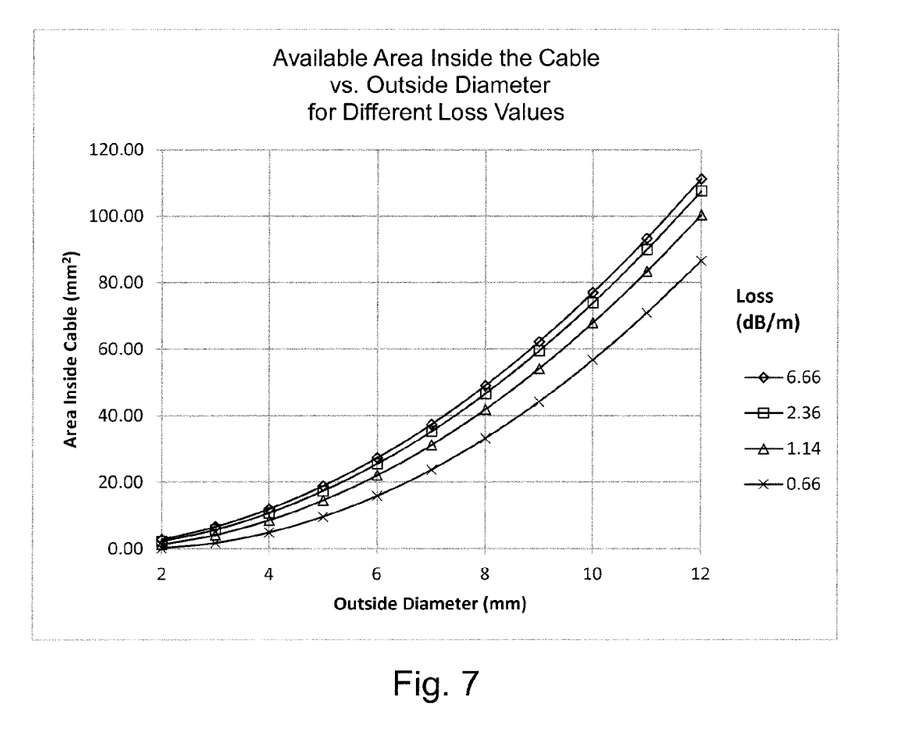
FIG. 7 is a graph showing how the usable area within a hollow coaxial energy conveying structure varies a function of outer diameter for different values of loss per metre.

FIG. 7 is a graph that shows the cross-sectional area within a coaxial transmission line of the type discussed above that is available for other components or channels of the insertion tube whilst achieved a certain level of loss performance. It demonstrates a important result of the effect of geometry of losses. That is that for a given outer diameter, a substantial portion of the internal volume of the coaxial transmission line is available even for very low losses. In particular, FIGS. 6 and 7 show the importance of not making the dielectric layer for the transmission line too thin. This means that a balance may need to be struck between making this layer thick enough to limit losses while being thin enough to leave room for other layers or the provide the required level of flexibility.

Figure 8A:
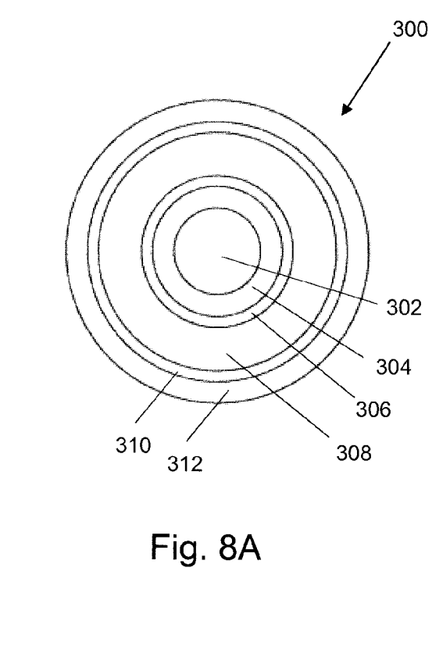
FIGS. 8A, 8B and 8C shows schematic cross-sectional view of three energy conveying liner geometries according to the invention, each of which are suitable for mounting in the instrument channel of an endoscope.
Figure 8B:
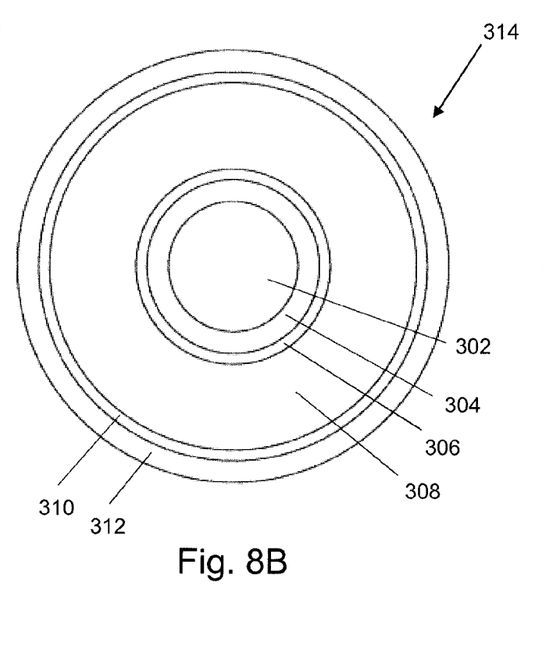
Figure 8C:
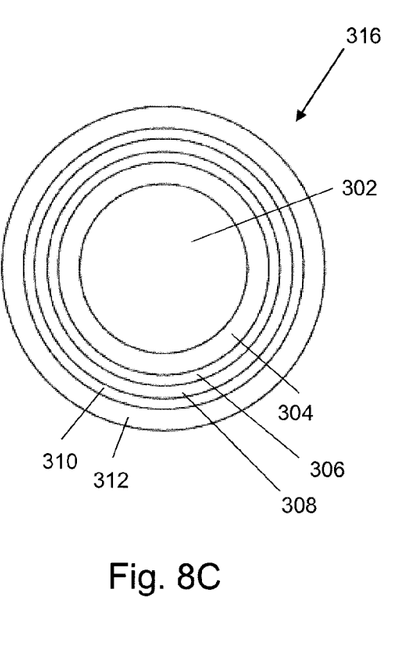

Similar principles regarding loss apply to the liner-type structure that can be mounted in the instrument channel of a scoping device. FIGS. 8A, 8B and 8C illustrate three possible geometries. FIG. 8A shows a cross-sectional view through a first liner-type coaxial transmission line 300 which has a hollow passage 302 running therethrough for receiving an electrosurgical instrument (not shown). The coaxial transmission line comprises an inner conductor 306 separated from an outer conductor 310 by a layer of dielectric material 308. An inner protective layer 302 is formed on the inner surface of the inner conductor 306 and thereby provides the surface of the hollow passage. An outer protective layer 312 is formed on the outer surface of the outer conductor 310 and engages the inner surface of the instrument channel.

FIG. 8B shows a cross-sectional view through a second liner-type coaxial transmission line 314. It has the same structure as FIG. 8A, so the same reference numbers are used.

FIG. 8C shows a cross-sectional view through a third liner-type coaxial transmission line 316. It also has the same structure as FIG. 8A, so the same reference numbers are used.

The table below describes the geometry of the structures shown in FIGS. 8A, 8B and 8C and lists corresponding values for loss per metre, impedance, loss over a typical cable length of 2.35 m and power delivered over such a cable (assuming a 60 W CW input power).

TABLE 1

Properties of liner-type coaxial transmission line structures

| | FIG. 8A | | FIG. 8B | | FIG. 8C | |
|---|---|---|---|---|---|---|
| Layer | Thickness (mm) | Diameter (mm) | Thickness (mm) | Diameter (mm) | Thickness (mm) | Diameter (mm) |
| 302 | — | 4 | — | 6 | — | 7.8 |
| 304 | 1 | 6 | 1 | 8 | 1 | 9.8 |
| 306 | 0.5 | 1 | 0.5 | 9 | 0.5 | 10.8 |
| 308 | 2 | 11 | 4 | 17 | 0.6 | 12 |
| 310 | 0.5 | 12 | 0.5 | 18 | 0.5 | 13 |
| 312 | 1 | 14 | 1 | 20 | 1 | 15 |
| Impedance (Ω) | 18.714 | | 26.332 | | 4.362 | |
| Loss per metre (dB/m) | 0.436 | | 0.280 | | 1.156 | |
| Loss* (dB) | 1.025 | | 0.658 | | 2.717 | |
| Power (W) | 47.390 | | 51.565 | | 32.099 | |

The invention claimed is:

1. An energy conveying structure for invasive electrosurgery, the energy conveying structure comprising a coaxial layered structure having:
    an innermost insulating layer;
    an inner conductive layer formed on the innermost insulating layer;
    an outer conductive layer formed coaxially with the inner conductive layer; and
    a dielectric layer separating the inner conductive layer and the outer conductive layer,
    wherein the inner conductive layer, the outer conductive layer and the dielectric layer form a transmission line for conveying radiofrequency (RF) and/or microwave energy,
    characterized in that:
    the coaxial layered structure is insertable in a flexible insertion tube of an invasive surgical scoping device,
    wherein the innermost insulating layer is hollow to form an instrument channel for the invasive surgical scoping device, and
    wherein the energy conveying structure includes:
        a first terminal that is electrically connected to the inner conductive layer and which extends through the innermost insulating layer into the instrument channel; and
        a second terminal that is electrically connected to the outer conductive layer and which extends through the dielectric layer and innermost insulating layer into the instrument channel.

2. An energy conveying structure according to claim 1, wherein the instrument channel has a diameter between 1 mm and 5 mm.

3. An energy conveying structure according to claim 1, wherein the first terminal is located proximally from the second terminal.

4. An electrosurgical device comprising:
    an energy conveying structure according to claim 1; and
    an electrosurgical instrument mounted in the instrument channel of the energy conveying structure, wherein the electrosurgical instrument comprises:
        a first contact that is electrically connectable to the first terminal;
        a second contact that is electrically connected to the second terminal;
        a distal bipolar transmission structure electrically connected to the first contact and the second contact for delivering the RF and/or microwave energy into biological tissue.

5. An electrosurgical device according to claim 4, wherein the distal bipolar transmission structure comprises a first conductive element that is electrically connected to the first contact and a second conductive element that is electrically connected to the first contact.

6. An electrosurgical device according to claim 5, wherein the first contact and the second contact are formed on a connection collar located proximally to the bipolar transmission structure.

7. An electrosurgical device according to claim 4 including a catheter for conveying a control wire or a fluid feed to the electrosurgical instrument, the catheter being slidably mounted in the instrument channel.

8. An electrosurgical device according to claim 6 including a catheter for conveying a control wire or a fluid feed to the electrosurgical instrument, the catheter being slidably mounted in the instrument channel, and wherein the connection collar is mounted on an outer surface of the catheter.

9. An electrosurgical device according to claim 6, wherein the connection collar includes a shoulder for abutting a projection at the distal end of the instrument channel.

10. An electrosurgical device according to claim 6 including an extension sleeve that extends axially away from the connection collar towards the bipolar transmission structure at the distal end of the electrosurgical instrument.

11. An electrosurgical device according to claim 10, wherein the extension sleeve comprises a tube of dielectric material, and carries a conductive structure which provides electrical connection between the first contact and first conductive element and between the second contact and second conductive element respectively.

12. An electrosurgical device according to claim 4, wherein a geometry of an interconnection between the electrosurgical instrument and the energy conveying structure is configured to create an impedance match between the electrosurgical instrument and the energy conveying structure at a frequency of microwave energy conveyed by the energy conveying structure.

13. An electrosurgical device according to claim 4, wherein the dielectric material is formed from polyimide.

14. An electrosurgical device according to claim 4, wherein the energy conveying structure comprises an additional conductor which forms a first pole of an RF-carrying bipolar transmission line, and wherein the inner conductive layer and the outer conductive layer form a second pole of the RF-carrying bipolar transmission line.

15. An electrosurgical device according to claim 14, wherein the additional conductor is a conductive wire carried within the instrument channel.

16. An invasive electrosurgical scoping device comprising:

a flexible insertion tube having a longitudinal bore formed therethrough;

an electrosurgical device according to claim 4 inserted in the longitudinal bore.

17. An invasive electrosurgical scoping device according to claim 16, wherein the flexible insertion tube includes a stop flange at its distal end, the stop flange having a projection that overhangs an entrance to the instrument channel.

18. An invasive electrosurgical scoping device according to claim 16, wherein the flexible insertion tube includes a resilient seal mounted over an entrance to the instrument channel.

19. An energy conveying structure according to claim 1, wherein the coaxial layered structure forms a liner that can be detachably mounted in a longitudinal bore of the flexible insertion tube of the invasive surgical scoping device.

20. An invasive electrosurgical scoping device comprising a body having a flexible insertion tube extending therefrom, wherein the flexible insertion tube comprises:

an observation channel formed therethrough, a longitudinal bore formed therethrough, and an energy conveying structure according to claim 1 integrally mounted in the longitudinal bore.

21. An invasive surgical scoping device comprising a body having a flexible insertion tube extending therefrom, wherein the flexible insertion tube comprises:

an observation channel formed therethrough, a longitudinal bore formed therethrough, and an energy conveying structure in the longitudinal bore, the energy conveying structure comprising a coaxial layered structure having:

an innermost insulating layer;

an inner conductive layer formed on the innermost insulating layer;

an outer conductive layer formed coaxially with the inner conductive layer; and a dielectric layer separating the inner conductive layer and the outer conductive layer, wherein the inner conductive layer, the outer conductive layer and the dielectric layer form a transmission line for conveying radiofrequency (RF) or microwave energy, and wherein the innermost insulating layer is hollow to form an instrument channel of the invasive surgical scoping device, and wherein at least the innermost insulating layer, the inner conductive layer and at least a portion of the dielectric layer form a liner that can be detachably mounted in the longitudinal bore.

22. An invasive surgical scoping device according to claim 21, wherein the outer conductive layer and a remaining portion of the dielectric layer are integrally formed in the wall of the longitudinal bore.

23. An invasive surgical scoping device according to claim 21, wherein the coaxial layered structure forms a liner that can be detachably mounted in the longitudinal bore.

* * * * *